United States Patent
Raman et al.

(10) Patent No.: US 9,993,422 B2
(45) Date of Patent: *Jun. 12, 2018

(54) IMMEDIATE RELEASE, ABUSE DETERRENT PHARMACEUTICAL COMPOSITIONS

(71) Applicant: Mallinckrodt LLC, Hazelwood, MO (US)

(72) Inventors: Siva N. Raman, St. Louis, MO (US); Jae Han Park, Olivette, MO (US); Thomas A. Diezi, Webster Groves, MO (US); Clifford J. Herman, St. Louis, MO (US); Sunil K. Battu, Manchester, MO (US); Eric A. Burge, Collinsville, IL (US)

(73) Assignee: SpecGX LLC, Webster Groves, MO (US)

( * ) Notice: Subject to any disclaimer, the term of this patent is extended or adjusted under 35 U.S.C. 154(b) by 1 day.

This patent is subject to a terminal disclaimer.

(21) Appl. No.: 13/865,286

(22) Filed: Apr. 18, 2013

(65) Prior Publication Data
US 2013/0280177 A1    Oct. 24, 2013

Related U.S. Application Data

(60) Provisional application No. 61/625,926, filed on Apr. 18, 2012, provisional application No. 61/792,478, filed on Mar. 15, 2013.

(51) Int. Cl.
*A61K 9/46* (2006.01)
*A61K 45/06* (2006.01)
*A61K 9/20* (2006.01)
*A61K 31/485* (2006.01)

(52) U.S. Cl.
CPC .......... *A61K 9/0007* (2013.01); *A61K 9/2031* (2013.01); *A61K 31/485* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 2,211,485 A * | 8/1940 | Zimmermann | 424/490 |
| 3,891,756 A | 6/1975 | Kasugai et al. | |
| 3,980,766 A | 9/1976 | Shaw et al. | |
| 4,070,494 A | 1/1978 | Hoffmeister et al. | |
| 4,678,661 A | 7/1987 | Gergely et al. | |
| 4,956,182 A | 9/1990 | Bequette | |
| 6,071,539 A * | 6/2000 | Robinson et al. | 424/466 |
| 6,200,604 B1 | 3/2001 | Pather et al. | |
| 6,264,981 B1 | 7/2001 | Zhang et al. | |
| 6,309,668 B1 | 10/2001 | Bastin et al. | |
| 6,340,471 B1 | 1/2002 | Kershman et al. | |
| 6,541,025 B1 | 4/2003 | Kershman et al. | |
| 6,713,089 B1 | 3/2004 | Bertelsen et al. | |
| 7,201,920 B2 | 4/2007 | Kumar et al. | |
| 7,510,726 B2 | 3/2009 | Kumar et al. | |
| 7,658,944 B2 | 2/2010 | Holm et al. | |
| 7,776,314 B2 | 8/2010 | Bartholomaus et al. | |
| 7,955,619 B2 | 6/2011 | Shah et al. | |
| 8,075,872 B2 | 12/2011 | Arkenau-Maric et al. | |
| 8,114,383 B2 | 2/2012 | Bartholomaus et al. | |
| 8,114,384 B2 | 2/2012 | Arkenau et al. | |
| 9,301,918 B2 | 4/2016 | Raman | |
| 2003/0068375 A1 | 4/2003 | Wright et al. | |
| 2004/0005359 A1 | 1/2004 | Cheng et al. | |
| 2005/0165038 A1 | 7/2005 | Gordon | |
| 2005/0236741 A1 | 10/2005 | Arkenau et al. | |
| 2005/0245557 A1 | 11/2005 | Schoenhard et al. | |
| 2006/0002860 A1 | 1/2006 | Bartholomaus et al. | |
| 2006/0193782 A1 | 8/2006 | Bartholomaus et al. | |
| 2007/0004795 A1 | 1/2007 | Sesha | |
| 2007/0048228 A1 | 3/2007 | Arkenau-Maric et al. | |
| 2007/0183980 A1 | 8/2007 | Arkenau-Maric et al. | |
| 2008/0102121 A1 | 5/2008 | Devane et al. | |
| 2008/0166405 A1 | 7/2008 | Mehta | |
| 2008/0247959 A1 | 10/2008 | Bartholomaus et al. | |
| 2008/0248113 A1 | 10/2008 | Bartholomaus et al. | |
| 2008/0280975 A1 | 11/2008 | Badul | |
| 2008/0311187 A1 | 12/2008 | Ashworth et al. | |
| 2009/0081290 A1 | 3/2009 | McKenna et al. | |
| 2009/0098200 A1 | 4/2009 | Temtsin Krayz et al. | |
| 2009/0124650 A1 | 5/2009 | Ahdieh | |
| 2009/0175937 A1 | 7/2009 | Rahmouni et al. | |
| 2009/0196922 A1 | 8/2009 | Guerrero et al. | |
| 2009/0221621 A1 | 9/2009 | Sathyan et al. | |
| 2009/0232887 A1 | 9/2009 | Odidi | |
| 2009/0317355 A1 | 12/2009 | Roth et al. | |
| 2010/0092553 A1 | 4/2010 | Guimberteau et al. | |

(Continued)

FOREIGN PATENT DOCUMENTS

AU    2013206525 A1    8/2013
EP    2123274    11/2009

(Continued)

OTHER PUBLICATIONS

Born et al. "Xanthan" (2002), downloaded from the internet at URL< http://www.wiley-vch.de/books/biopoly/pdf_v05/bpol5011_259_269.pdf >.*

(Continued)

*Primary Examiner* — Abigail Vanhorn
*Assistant Examiner* — Daniel L Branson

(57) ABSTRACT

The present disclosure provides pharmaceutical compositions and processes for making solid dosage form pharmaceutical compositions that provide immediate release of active ingredients and have abuse deterrent properties. The pharmaceutical compositions provided herein comprise at least one pharmaceutically active ingredient, at least one low molecular weight hydrophilic polymer, at least one high molecular weight hydrophilic polymer, and an effervescent system.

18 Claims, 3 Drawing Sheets

(56) References Cited

U.S. PATENT DOCUMENTS

| | | |
|---|---|---|
| 2010/0151028 A1 | 6/2010 | Ashworth et al. |
| 2010/0166858 A1 | 7/2010 | Mehta et al. |
| 2010/0168148 A1 | 7/2010 | Wright et al. |
| 2010/0204259 A1 | 8/2010 | Tygesen |
| 2010/0260833 A1 | 10/2010 | Bartholomaus et al. |
| 2011/0020451 A1 | 1/2011 | Bartholomaus et al. |
| 2011/0054038 A1 | 3/2011 | Glozman |
| 2011/0117196 A1 | 5/2011 | Gordon |
| 2011/0165248 A1 | 7/2011 | Machonis |
| 2011/0268666 A1 | 11/2011 | Friedman et al. |
| 2012/0028937 A1 | 2/2012 | Tsuzuki et al. |
| 2012/0136021 A1 | 5/2012 | Barnscheid et al. |
| 2012/0214777 A1 | 8/2012 | Crowley et al. |
| 2012/0321674 A1 | 12/2012 | Vachon et al. |
| 2012/0321716 A1 | 12/2012 | Vachon et al. |
| 2013/0280176 A1 | 10/2013 | Diezi et al. |
| 2013/0280177 A1 | 10/2013 | Raman et al. |
| 2014/0017310 A1 | 1/2014 | Gower et al. |
| 2016/0000703 A1 | 1/2016 | Micka et al. |

FOREIGN PATENT DOCUMENTS

| | | |
|---|---|---|
| EP | 2161021 A1 | 3/2010 |
| JP | 62-089616 | 4/1987 |
| JP | 2011105615 A | 6/2011 |
| WO | 2002/019987 A1 | 3/2002 |
| WO | 03/032954 A1 | 4/2003 |
| WO | 2007/009806 A2 | 1/2007 |
| WO | 2008/011595 A2 | 1/2008 |
| WO | 2008/033523 A1 | 3/2008 |
| WO | 2008/039737 A2 | 4/2008 |
| WO | 2008/086804 A2 | 7/2008 |
| WO | 2008/128191 A2 | 10/2008 |
| WO | 2009/092601 A1 | 7/2009 |
| WO | 2011/066980 A2 | 6/2011 |
| WO | 2011079074 | 6/2011 |
| WO | 2012/028318 A1 | 3/2012 |
| WO | 2012/112952 A1 | 8/2012 |
| WO | 2013/077851 A1 | 5/2013 |
| WO | 2013/158810 A1 | 10/2013 |
| WO | 2013/158814 A1 | 10/2013 |
| WO | 2014/011830 A1 | 1/2014 |
| WO | 2016/004170 A1 | 1/2016 |

OTHER PUBLICATIONS

Polyox water soluble resins, [online], (2002), downloaded from the internet from URL <http://msdssearch.dow.com/PublishedLiteratureDOWCOM/dh_0031/0901b80380031a4a.pdf?filepath=/326-00001.pdf&fromPage=GetDoc>.*
International Search Report and Written Opinion from related International Patent Application No. PCT/US2013/037056, dated Jun. 24, 2013; 9 pgs.
International Search Report and Written Opinion from related International Patent Application No. PCT/US2013/037046, dated Jul. 3, 2013; 12 pgs.
International Search Report and Written Opinion from related International Patent Application No. PCT/US2013/050005, dated Aug. 19, 2013; 12 pgs.
Usui et al., "Interactions in the Solid State 1: Interactions of Sodium Bicarbonate and Tartaric Acid under Compressed Conditions," J. Pharm. Sci.,1985, pp. 1293-1297, vol. 74, No. 12.
Beer Beate et al.: "Impact of slow-release oral morphine on drug abusing habits in Austria", Neuropsychiatrie, Dustri Verlag, Deisenhofen, DE, vol. 24, No. 2; Jan. 1, 2010; pp. 108-117.

Opadry II Application Data, The Effect of Coating Process Conditions and Coating Formula Type on the Quantity and Location of Water in Film Coated Tablets, Colorcon, 2009, 5 pages.
Office action dated Feb. 19, 2016 from related CA Application No. 2,864,738, 5 pgs.
Office action dated Mar. 7, 2016 from related JP Application No. 2015-507160, 11 pgs.
Office action dated Oct. 7, 2015 from related U.S. Appl. No. 13/865,244, 9 pgs.
Office action dated Mar. 10, 2015 from related U.S. Appl. No. 14/211,307, 6 pgs.
Office action dated Aug. 19, 2015 from related U.S. Appl. No. 14/211,307, 10 pgs.
Final Office action dated Mar. 15, 2016 from related U.S. Appl. No. 14/788,908, 16 pgs.
International Search Report and Written Opinion dated Oct. 6, 2015 from related International Application No. PCT/US15/38774, 8 pgs.
Office action dated Nov. 24, 2015 from related U.S. Appl. No. 14/788,908, 9 pgs.
Notice of Allowance dated Jan. 12, 2017 from related CA Application No. 2,864,738, 1 pg.
Notice of Allowance dated Feb. 22, 2017 from related JP Application No. 2015-507158, 5 pgs.
Intent to Grant dated Mar. 9, 2017 from related EP Application No. 13719340.5, 62 pgs.
Apr. 2, 2017 Letter from IL associate regarding Office action dated Feb. 13, 2017 from related IL Application No. 234996, 2 pgs.
Apr. 4, 2017 Letter from IL associate regarding Office action dated Feb. 19, 2017 from related IL Application No. 234997, 3 pgs.
Office action dated Jul. 5, 2016 from related CA Application No. 2,868,416, 4 pgs.
Office action dated Jul. 12, 2016 from related JP Application No. 2015-507160, 7 pgs.
Office action dated Oct. 19, 2016 from related JP Application No. 2015-507158, 7 pgs.
Office action dated Nov. 9, 2016 from related EP Application No. 13719672.1, 6 pgs.
Dec. 8, 2016 Letter from JP associate regarding Notice of Allowance dated Dec. 8, 2016 from related JP Application No. 2015-507160, 6 pgs.
Office action dated Dec. 1, 2016 from related U.S. Appl. No. 13/865,244, 10 pgs.
Bhatt et al., "Pharmaceutical Engineering: Mixing," 2007, pp. 1-24, <nsdl.niscair.res.in/jspui/bitstream/123456789/751/1/Revised%20mixing.pdf>.
Final Office action dated Jun. 16, 2017 from related U.S. Appl. No. 13/865,244, 9 pp.
Jun. 1, 2017 Letter from Associate regarding Mexican Office action dated May 28, 2017, 3 pp.
Shah, "Polyox (Polyethylene Oxide) Multifunctional Polymer in Novel Drug Delivery System." Int. J. Pharmaceut Sci. and Drug Res., 2014, 6(2):95-101.
Office action dated May 20, 2016 from related U.S. Appl. No. 13/865,244, 10 pgs.
Office action dated Apr. 20, 2016 from related JP Application No. 2015-507158, 12 pgs.
Office action dated Jul. 21, 2016 from related U.S. Appl. No. 14/788,908, 26 pp.
Office action dated Jan. 19, 2017 from related U.S. Appl. No. 14/788,908, 21 pp.
Office action dated May 16, 2017 from related U.S. Appl. No. 14/788,908, 15 pp.
Office action dated Sep. 25, 2017 from related U.S. Appl. No. 14/788,908, 23 pp.

* cited by examiner

IMMEDIATE RELEASE, ABUSE DETERRENT PHARMACEUTICAL COMPOSITIONS

CROSS-REFERENCE TO RELATED APPLICATIONS

This application claims the benefit of U.S. Provisional Application No. 61/625,926 filed Apr. 18, 2012, and U.S. Provisional Application No. 61/792,478 filed Mar. 15, 2013 each of which is incorporated by reference herein in its entirety.

FIELD OF THE INVENTION

The present disclosure generally relates to pharmaceutical compositions that provide immediate release of active ingredients and have abuse deterrent properties.

BACKGROUND OF THE INVENTION

Abuse of prescription drugs (particularly opioids) has become a serious societal problem. Such abuse places an enormous economic burden on society due to increased health care, work place, and criminal justice costs. Several routes of administration are commonly attempted by abusers. For example, the oral solid dosage form may be crushed or pulverized into a powder and administered intranasally (i.e., snorted) or dissolved in a suitable solvent (e.g., water) and administered parenterally (i.e., injected intravenously).

Attempts have been made to diminish the abuse of opioid solid dosage forms. One approach has been to include in the dosage form an opioid antagonist that is not orally active but will substantially block the analgesic effects of the opioid if one attempts to dissolve the opioid and administer it parenterally. Another approach has been to include gel-forming high molecular weight polymers that confer plasticity to the dosage form rendering them difficult to crush and pulverize into a powder. These high molecular weight polymers, however, retard the release of the active ingredient from the dosage forms, making them unsuitable for immediate release formulations.

Thus, there is a need for oral solid dosage forms that provide immediate release of the active ingredient yet are resistant to abuse.

SUMMARY OF THE INVENTION

Among the various aspects of the present disclosure is the provision of a pharmaceutical composition comprising at least one active pharmaceutical ingredient (API) or a pharmaceutically acceptable salt thereof, at least one low molecular weight hydrophilic polymer, at least one high molecular weight hydrophilic polymer, and an effervescent system. The pharmaceutical composition provides immediate release of the API and is abuse deterrent.

A further aspect of the present disclosure provides a process for preparing a solid dosage form. The process comprises forming a mixture comprising at least one low molecular weight hydrophilic polymer, at least one high molecular weight hydrophilic polymer, and an effervescent system. The process further comprises forming the mixture into a solid dosage unit, and heating the solid dosage unit to yield the solid dosage form.

Other aspects and iterations of the disclosure are described in more detail below.

DETAILED DESCRIPTION OF THE INVENTION

Figure 1A:
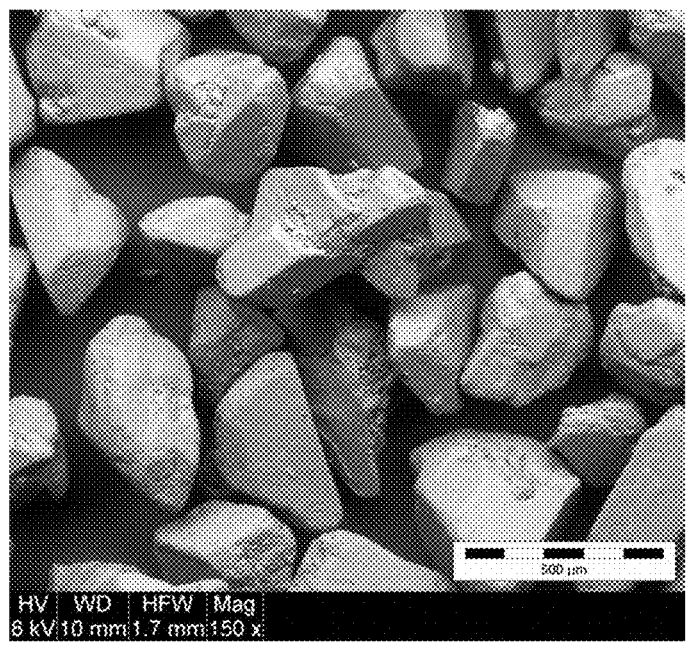
FIG. 1A presents SEM image of L-(+)-tartaric acid particles.
Figure 1B:
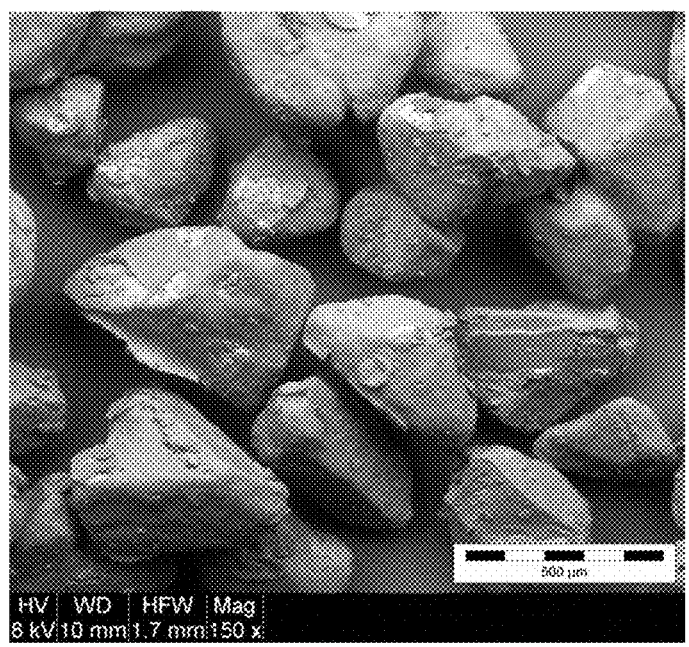
FIG. 1B presents SEM image of L-(+)-tartaric acid particles coated with Pluronic F127.
Figure 1C:
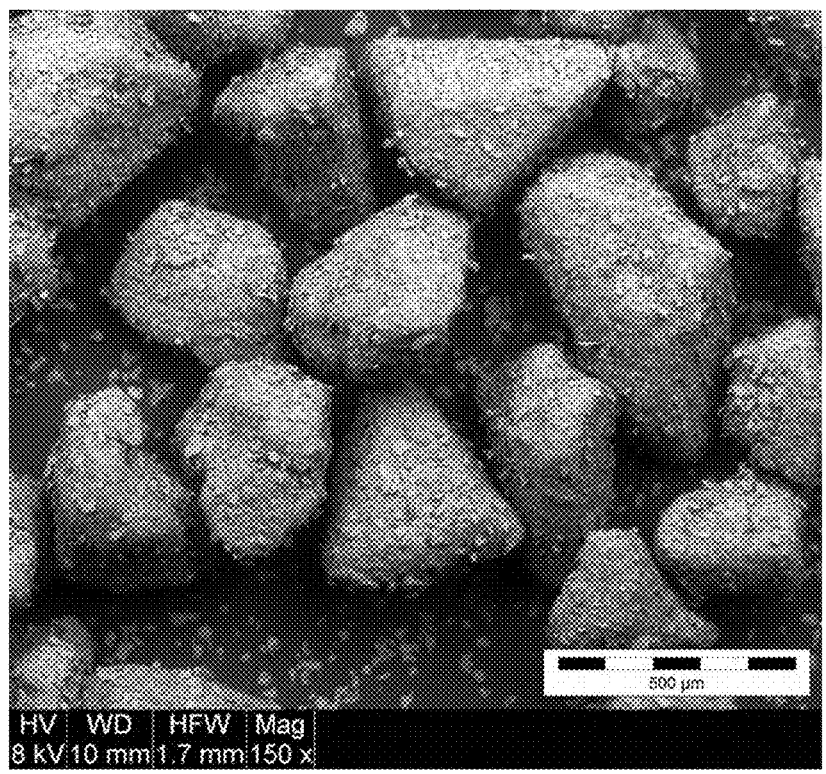
FIG. 1C presents SEM image of Pluronic F127-coated L-(+)-tartaric acid particles blended with talc.
Figure 2A:
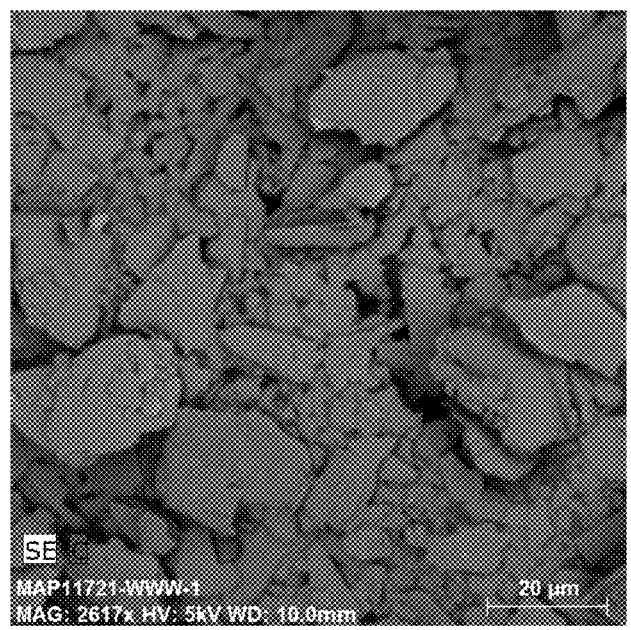
FIG. 2A and FIG. 2B show the surface of Pluronic F127-coated tartaric acid particles blended with talc. Elemental mapping shows that the majority of the surface is covered with talc, with limited Pluronic F127-coated surface visible.
Figure 2B:
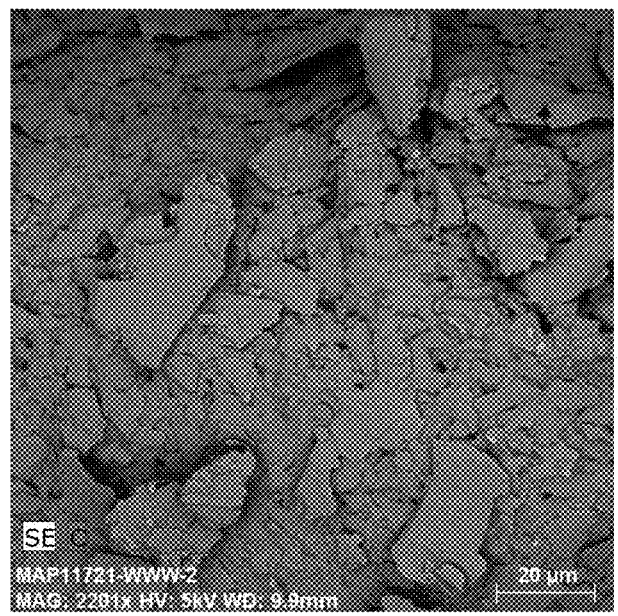

The present disclosure provides pharmaceutical compositions and processes for making solid dosage pharmaceutical compositions that provide rapid release of the active ingredients and have abuse deterrent properties. In particular, the pharmaceutical compositions comprise a combination of low and high molecular weight hydrophilic polymers and an effervescent system comprising an acid component and a base component. It was unexpectedly discovered that the combination of low and high molecular weight hydrophilic polymers and the effervescent system makes the compositions resistant to crushing into fine powders and/or extracting with suitable solvents, while still providing immediate release of the active ingredients.

(I) Pharmaceutical Compositions

One aspect of the present disclosure provides abuse deterrent pharmaceutical compositions that provide immediate release of the active pharmaceutical ingredients. Detailed below are the components of the composition, dosage forms of the composition, release characteristics of the composition, and abuse deterrent properties of the composition.

(a) Components of the Pharmaceutical Composition

The pharmaceutical compositions disclosed herein comprise at least one low molecular weight hydrophilic polymer, at least one high molecular weight hydrophilic polymer, and an effervescent system. The combination of hydrophilic polymers of different molecular sizes and the effervescent system yields a functional abuse deterrent, immediate release composition.

(i) Hydrophilic Polymers

The pharmaceutical compositions disclosed herein comprise hydrophilic polymers of different molecular weights. The term "hydrophilic polymer" refers to a polymer with affinity for water such that it readily absorbs and/or dissolves in water or an aqueous solution. Hydrophilic polymers may be soluble in water or an aqueous solution and/or swellable in water or an aqueous solution. Polymers that swell in water or an aqueous solution may be termed gelling polymers.

A variety of hydrophilic polymers are suitable for use in the pharmaceutical compositions. The hydrophilic polymer may be natural, semi-synthetic, or synthetic. In some embodiments, the hydrophilic polymer may be a polyalkylene oxide such as polyethylene oxide (PEO), polypropylene oxide, combinations thereof, or copolymers thereof. In other embodiments, the hydrophilic polymer may be a cellulose ether, which is a cellulose derivative in which the hydrogen atoms of hydroxyl groups are replaced with alkyl groups. Non-limiting examples of suitable cellulose ethers include hydroxypropyl cellulose (HPC), hydroxypropylmethyl cellulose (HPMC), carboxymethyl cellulose (CMC), methyl cellulose, hydroxyethyl cellulose, hydroxyethylmethyl cellulose, and the like. In still other embodiments, the hydrophilic polymer may be a polyalkylene glycol such as polyethylene glycol (PEG) (e.g., PEG 1000, PEG 2000, PEG 4000, PEG 6000, PEG 8000, PEG 10,000, PEG 20,000, PEG 30,000), derivatives thereof, combinations thereof, and copolymers thereof. In further embodiments, the hydrophilic polymer may be a Poloxamer, which is a difunctional, tri-block copolymer of ethylene oxide and polyproplylene oxide (available under the tradenames KOLLIPHOR™ or PLURONIC®). Available Poloxamers include Poloxamers 101, 105, 108, 122, 123, 124, 181, 182, 183, 184, 185, 188, 212, 215, 217, 231, 234, 235, 237, 238, 282, 284, 288, 331, 333, 334, 335, 338, 401, 402, 403, and 407, wherein the first two digits multiplied by 100 give the approximate molecular mass and the last digit multiplied by 10 gives the percentage of the polyoxyethylene oxide content. In one embodiment, the hydrophilic polymer may be Poloxamer 407. In still other embodiments, the hydrophilic polymer may be a polysaccharide. Suitable polysaccharides include, without limit, celluloses, starches, pectins, chitins, gums (i.e., polysaccharides derived from plants or microbes), combinations thereof, and derivatives thereof. Non-limiting examples of suitable gums include xanthan gum, acacia gum, diutan gum, gellan gum, guar gum, fenugreek gum, locust bean gum, pullulan, welan gum, or combinations thereof. In additional embodiments, the hydrophilic polymer may be a polycarboxylic acid such as polyacrylic acid, polyacrylic acid-co-acrylamide, polymethacrylate, polyhydroxyethyl methacrylate, combinations, or copolymers thereof. In other embodiments, the hydrophilic polymer may be a polyamine such as polyethyleneimine, polyvinylamine, or the like. In further embodiments, the hydrophilic polymer may be a polypeptide such as gelatin, albumin, polylysine, soy protein, and so forth. In still further embodiments, the hydrophilic polymer may be a polyolefinic alcohol (such as polyvinyl alcohol), or a polyvinyl lactam (such as, e.g., polyvinylpyrrolidone, polyvinyl caprolactam, and the like). The hydrophilic polymer also may be a combination or a copolymer of any of the foregoing.

(ii) Low Molecular Weight Hydrophilic Polymer

The pharmaceutical composition comprises at least one low molecular weight hydrophilic polymer. As used herein, the term "low molecular weight polymer" refers to a polymer having an average molecular weight of no more than about 200,000 Da. In various embodiments, the average molecular weight of the low molecular weight polymer may range from about 200,000 to about 175,000 Da, from about 175,000 to about 150,000 Da, from about 150,000 to about 125,000 Da, from about 125,000 to about 100,000 Da, from about 100,000 to about 75,000 Da, from about 75,000 to about 50,000 Da, from about 50,000 to about 25,000 Da, or from about 25,000 to about 1000 Da. In some embodiments, the pharmaceutical composition may comprise a hydrophilic polymer having an average molecular weight of about 100,000 Da or less. In other embodiments, the pharmaceutical composition may comprise a hydrophilic polymer having an average molecular weight of about 30,000 Da or less. In further embodiments, the pharmaceutical composition may comprise a hydrophilic polymer having an average molecular weight of about 10,000 Da or less.

In one embodiment, the pharmaceutical composition comprises one hydrophilic polymer having an average molecular weight of no more than about 200,000 Da. In another embodiment, the pharmaceutical composition comprises two hydrophilic polymers, the average molecular weight of each being no more than about 200,000 Da. In still another embodiment, the pharmaceutical composition comprises three hydrophilic polymers, the average molecular weight of each being no more than about 200,000 Da. In a further embodiment, the pharmaceutical composition comprises four hydrophilic polymers, the average molecular weight of each being no more than about 200,000 Da. In yet another embodiment, the pharmaceutical composition comprises five hydrophilic polymers, the average molecular weight of each being no more than about 200,000 Da. Examples of suitable hydrophilic polymers are detailed above in section (I)(a)(i).

In one embodiment, the pharmaceutical composition comprises polyethylene oxide having an average molecular weight of about 100,000 Da. In another embodiment, the pharmaceutical composition comprises hydroxypropylmethyl cellulose having an average molecular weight of about 100,000 Da. In still another embodiment, the pharmaceutical composition comprises (sodium) carboxymethyl cellulose having an average molecular weight of about 90,000 Da or less. In a further embodiment, the pharmaceutical composition comprises polyethylene glycol having an average molecular weight of about 20,000 Da or less. In yet another embodiment, the pharmaceutical composition comprises a Poloxamer having an average molecular weight of about 10,000 Da or less. In further embodiments, the pharmaceutical composition comprises two or more of the specific above-cited polymers.

The amount of the low molecular weight hydrophilic polymer present in the pharmaceutical composition can and will vary depending upon the desired properties of the composition, as well as the identity and amounts of other components present in the composition. In general, the amount of the low molecular weight hydrophilic polymer present may range from about 5% to about 50% by weight of the pharmaceutical composition. In various embodiments, the amount of the low molecular weight hydrophilic polymer present in the composition may range from about 5% to about 10%, from about 10% to about 15%, from about 15% to about 20%, from about 20% to about 25%, from about 25% to about 30%, from about 30% to about 40%, or from about 40% to about 50% by weight of the pharmaceutical composition. In one embodiment, the amount of the low molecular weight polymer present in the composition may range from about 10% to about 40% by weight of the pharmaceutical composition. In an exemplary embodiment, the amount of the low molecular weight polymer present may range from about 20% to about 35% by weight of the pharmaceutical composition.

(iii) High Molecular Weight Hydrophilic Polymer

The pharmaceutical composition disclosed herein also comprises at least one high molecular weight hydrophilic polymer. A "high molecular weight polymer," as used herein, refers to a polymer having an average molecular weight of at least about 400,000 Da. In general, the average molecular weight of the high molecular weight polymer may range from about 400,000 to about 15,000,000 Da. For example, the high molecular weight polymer may have an average molecular weight that ranges from about 400,000 to about 600,000 Da, from about 600,000 to about 800,000 Da, from about 800,000 to 1,000,000 Da, from about 1,000,000 to about 4,000,000 Da, from about 4,000,000 to about 8,000,000 Da, from about 8,000,000 to about 12,000,000 Da, or from about 12,000,000 to about 15,000,000 Da. In some embodiments, the pharmaceutical composition may comprise a hydrophilic polymer having an average molecular weight of at least about 4,000,000 Da. In other embodiments, the pharmaceutical composition may comprise a hydrophilic polymer having an average molecular weight of at least about 1,000,000 Da. In further embodiments, the pharmaceutical composition may comprise a hydrophilic polymer having an average molecular weight of at least about 800,000 Da.

In one embodiment, the pharmaceutical composition comprises one hydrophilic polymer having an average molecular weight of at least about 400,000 Da. In another embodiment, the pharmaceutical composition comprises two hydrophilic polymers, the average molecular weight of each being at least about 400,000 Da. In still another embodiment, the pharmaceutical composition comprises three hydrophilic polymers, the average molecular weight of each being at least about 400,000 Da. In a further embodiment, the pharmaceutical composition comprises four hydrophilic polymers, the average molecular weight of each being at least about 400,000 Da. Examples of suitable hydrophilic polymers are detailed above in section (I)(a)(i).

In one embodiment, the pharmaceutical composition comprises polyethylene oxide having an average molecular weight of at least about 1,000,000 Da. In another embodiment, the pharmaceutical composition comprises polyethylene oxide having an average molecular weight of about 4,000,000 Da. In a further embodiment, the pharmaceutical composition comprises xanthan gum having an average molecular weight of at least about 1,000,000 Da. In still another embodiment, the pharmaceutical composition comprises hydroxypropyl cellulose having an average molecular weight of at least about 800,000 Da. In further embodiments, the pharmaceutical composition comprises two or more of the specific above-cited polymers.

The amount of the high molecular weight hydrophilic polymer present in the pharmaceutical composition can and will vary depending upon the desired properties of the composition, as well as the identity and amounts of other components present in the composition. In general, the amount of the high molecular weight polymer present in the composition may range from about 0.1% to about 30% by weight of the composition. In various embodiments, the amount of the high molecular weight polymer present in the composition may range from about 0.1% to about 0.3%, from about 0.3% to about 1%, from about 1% to about 3%, from about 3% to about 10%, or from about 10% to about 30% by weight of the pharmaceutical composition. In one embodiment, the amount of the high molecular weight hydrophilic polymer present in the composition may range from about 1% to about 15% by weight of the pharmaceutical composition. In an exemplary embodiment, the amount of the high molecular weight hydrophilic polymer present in the composition may range from about 2% to about 10% by weight of the pharmaceutical composition.

(iv) Effervescent System

The pharmaceutical compositions disclosed herein also comprise an effervescent system. As used herein, an "effervescent system" refers to a system generally comprising an acid component and a base component, wherein the system liberates carbon dioxide upon contact with an aqueous solution. Without being bound by any particular theory, it is believed that the effervescent system facilitates rapid dissolution of the API from a composition comprising the combination of low and high molecular weight hydrophilic polymers.

The acid component of the effervescent system may be an organic acid, an inorganic acid, or a combination thereof. Non-limiting examples of suitable acids include adipic acid, ascorbic acid, benzoic acid, citric acid, fumaric acid, glutaric acid, lactic acid, lauric acid, malic acid, maleic acid, malonic acid, oxalic acid, phthalic acid, sorbic acid, succinic acid, tartaric acid, ammonium phosphate, potassium bitartrate, potassium phosphate, dipotassium phosphate, disodium pyrophosphate, sodium acid pyrophosphate, sodium phosphate, disodium phosphate, and combinations thereof. In exemplary embodiments, the acid component of the effervescent system may be an organic acid. In one exemplary embodiment, the acid component may be tartaric acid. In other embodiments, the acid component of the effervescent system may be an inorganic acid.

In some embodiments, the acid component of the effervescent system may be co-processed with a polyalkylene glycol or a Poloxamer. Suitable polyalkylene glycols and Poloxamers are detailed above in section (I)(a)(i). The acid and the polyalkylene glycol/Poloxamer may be co-processed by a variety of means including, without limit, hot melt granulation, fluidized hot melt granulation, hot melt mixing, wet granulation, liquid spray mixing, and the like. The amount of polyalkylene glycol/Poloxamer co-processed with the acid can and will vary. In general, the weight to weight ratio of the acid to the polyalkylene glycol/Poloxamer may range from about 1:0.01 to about 1:0.5.

The base component of the effervescent system may be a bicarbonate, a carbonate, or a combination thereof. In various embodiments, the base component may be an alkali metal bicarbonate, an alkaline earth metal bicarbonate, an alkali metal carbonate, an organic carbonate, or combinations thereof. Non-limiting examples of suitable bases include ammonium bicarbonate, calcium bicarbonate, lithium bicarbonate, magnesium bicarbonate, potassium bicarbonate, sodium bicarbonate, arginine carbonate, ammonium carbonate, calcium carbonate, lysine carbonate, potassium magnesium carbonate, sodium carbonate, sodium glycine carbonate, sodium sesquicarbonate, zinc carbonate, and combinations thereof. In exemplary embodiments, the base component of the effervescent system may be an alkali metal bicarbonate. In one exemplary embodiment, the base component may be sodium bicarbonate. In another exemplary embodiment, the base component may be heat-treated sodium bicarbonate (for example EfferSoda® 12).

The mole to mole ratio of the acid component to the base component in the effervescent system may also vary depending, for example, upon the identity of the acid and the base components. In general, the mole to mole ratio of the acid component to the base component in the effervescent system may range from about 1:0.2 to about 1:5. For example, the mole to mole ratio of the acid component to the base component in the effervescent system may be about 1:0.2, about 1:0.25, about 1:0.33, about 1:0.5, about 1:1, about 1:2, about 1:3, about 1:4, about 1:5 or any ratio in between. In one exemplary embodiment, the mole to mole ratio of the acid component to the base component in the effervescent system may range from about 1:1 to about 1:3. In another exemplary embodiment, the mole to mole ratio of the acid component to the base component in the effervescent system may be about 1:2.

The amount of the effervescent system present in the composition can and will vary depending upon the identity of the other components and the desired properties of the composition. In general, the amount of the effervescent system present in the composition may range from about 20% to about 90% by weight of the composition. In various embodiments, the amount of the effervescent system present in the composition may be from about 20% to about 30%, from about 30% to about 40%, from about 40% to about 50%, from about 50% to about 60%, from about 60% to about 70%, from about 70% to about 80%, or from about 80% to about 90% by weight of the pharmaceutical composition. In certain embodiments, the amount of the effervescent system present in the composition may range from about 40% to about 80% by weight of the pharmaceutical composition. In one exemplary embodiment, the amount of the effervescent system present in the composition may range from about 50% to about 70% by weight of the pharmaceutical composition.

(v) API

The pharmaceutical composition disclosed herein comprises at least one API or salt thereof. Suitable APIs include, without limit, opioid analgesic agents (e.g., adulmine, alfentanil, allocryptopine, allylprodine, alphaprodine, anileridine, aporphine, benzylmorphine, berberine, bicuculine, bicucine, bezitramide, buprenorphine, bulbocaprine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, nalorphine, nalbuphene, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propoxyphene, sufentanil, tapentadol, tilidine, and tramadol); non-opioid analgesic agents (e.g., acetylsalicylic acid, acetaminophen, paracetamol, ibuprofen, ketoprofen, indomethacin, diflunisol, naproxen, ketorolac, dichlophenac, tolmetin, sulindac, phenacetin, piroxicam, and mefamanic acid); anti-inflammatory agents (e.g., glucocorticoids such as alclometasone, fluocinonide, methylprednisolone, triamcinolone and dexamethasone; non-steroidal anti-inflammatory agents such as celecoxib, deracoxib, ketoprofen, lumiracoxib, meloxicam, parecoxib, rofecoxib, and valdecoxib); antitussive agents (e.g., dextromethorphan, codeine, hydrocodone, caramiphen, carbetapentane, and dextromethorphan); antipyretic agents (e.g., acetylsalicylic acid and acetaminophen); antibiotic agents (e.g., aminoglycosides such as, amikacin, gentamicin, kanamycin, neomycin, netilmicin, streptomycin, and tobramycin; carbecephem such as loracarbef; carbapenems such as certapenem, imipenem, and meropenem; cephalosporins such as cefadroxil cefazolin, cephalexin, cefaclor, cefamandole, cephalexin, cefoxitin, cefprozil, cefuroxime, cefixime, cefdinir, cefditoren, cefoperazone, cefotaxime, cefpodoxime, ceftazidime, ceftibuten, ceftizoxime, and ceftriaxone; macrolides such as azithromycin, clarithromycin, dirithromycin, erythromycin, and troleandomycin; monobactam; penicillins such as amoxicillin, ampicillin, carbenicillin, cloxacillin, dicloxacillin, nafcillin, oxacillin, penicillin G, penicillin V, piperacillin, and ticarcillin; polypeptides such as bacitracin, colistin, and polymyxin B; quinolones such as ciprofloxacin, enoxacin, gatifloxacin, levofloxacin, lomefloxacin, moxifloxacin, norfloxacin, ofloxacin, and trovafloxacin; sulfonamides such as mafenide, sulfacetamide, sulfamethizole, sulfasalazine, sulfisoxazole, and trimethoprim-sulfamethoxazole; tetracyclines such as demeclocycline, doxycycline, minocycline, and oxytetracycline); antimicrobial agents (e.g., ketoconazole, amoxicillin, cephalexin, miconazole, econazole, acyclovir, and nelfinavir); antiviral agents (e.g., acyclovir, gangciclovir, oseltamivir, and relenza); steroids (e.g., estradiol, testosterone, cortisol, aldosterone, prednisone, and cortisone); amphetamine stimulant agents (e.g., amphetamine and amphetamine-like drugs); non-amphetamine stimulant agents (e.g., methylphenidate, nicotine, and caffeine); laxative agents (e.g., bisacodyl, casanthranol, senna, and castor oil); anti-nausea agents (e.g., dolasetron, granisetron, ondansetron, tropisetron, meclizine, and cyclizine); anorexic agents (e.g., fenfluramine, dexfenfluramine, mazindol, phentermine, and aminorex); antihistaminic agents (e.g., phencarol, cetirizine, cinnarizine, ethamidindole, azatadine, brompheniramine, hydroxyzine, and chlorpheniramine); antiasthmatic agents (e.g., zileuton, montelukast, omalizumab, fluticasone, and zafirlukast); antidiuretic agents (e.g., desmopressin, vasopressin, and lypressin); antimigraine agents (e.g., naratriptan, frovatriptan, eletriptan, dihydroergotamine, zolmitriptan, almotriptan, and sumatriptan); antispasmodic agents (e.g., dicyclomine, hyoscyamine, and peppermint oil); antidiabetic agents (e.g., methformin, acarbose, miglitol, pioglitazone, rosiglitazone, nateglinide, repaglinide, mitiglinide, saxagliptin, sitagliptine, vildagliptin, acetohexamide, chlorpropamide, gliclazide, glimepiride, glipizide, glyburide, tolazamide, and tolbutamide); respiratory agents (e.g., albuterol, ephedrine, metaproterenol, and terbutaline); sympathomimetic agents (e.g., pseudoephedrine, phenylephrine, phenylpropanolamine, epinephrine, norepinephrine, dopamine, and ephedrine); H2 blocking agents (e.g., cimetidine, famotidine, nizatidine, and ranitidine); antihyperlipidemic agents (e.g., clofibrate, cholestyramine, colestipol, fluvastatin, atorvastatin, genfibrozil, lovastatin, niacin, pravastatin, fenofibrate, colesevelam, and simvastatin); antihypercholesterol agents (e.g., lovastatin, simvastatin, pravastatin, fluvastatin, atorvastatin, cholestyramine, colestipol, colesevelam, nicotinic acid, gemfibrozil, and ezetimibe); cardiotonic agents (e.g., digitalis, ubidecarenone, and dopamine); vasodilating agents (e.g., nitroglycerin, captopril, dihydralazine, diltiazem, and isosorbide dinitrate); vasoconstricting agents (e.g., dihydroergotoxine and dihydroergotamine); anticoagulants (e.g., warfarin, heparin, and Factor Xa inhibitors); sedative agents (e.g., amobarbital, pentobarbital, secobarbital, clomethiazole, diphenhydramine hydrochloride, and alprazolam); hypnotic agents (e.g., zaleplon, zolpidem, eszopiclone, zopiclone, chloral hydrate, and clomethiazole); anticonvulsant agents (e.g., lamitrogene, oxycarbamezine, phenytoin, mephenytoin, ethosuximide, methsuccimide, carbamazepine, valproic acid, gabapentin, topiramate, felbamate, and phenobarbital); muscle relaxing agents (e.g., baclofen, carisoprodol, chlorzoxazone, cyclobenzaprine, dantrolene sodium, metaxalone, orphenadrine, pancuronium bromide, and tizanidine); antipsychotic agents (e.g., phenothiazine, chlorpromazine, fluphenazine, perphenazine, prochlorperazine, thioridazine, trifluoperazine, haloperidol, droperidol, pimozide, clozapine, olanzapine, risperidone, quetiapine, ziprasidone, melperone, and paliperidone); antianxiolitic agents (e.g., lorazepam, alprazolam, clonazepam, diazepam, buspirone, meprobamate, and flunitrazepam); antihyperactive agents (e.g., methylphenidate, amphetamine, and dextroamphetamine); antihypertensive agents (e.g., alpha-methyldopa, chlortalidone, reserpine, syrosingopine, rescinnamine, prazosin, phentolamine, felodipine, propanolol, pindolol, labetalol, clonidine, captopril, enalapril, and lisonopril); anti-neoplasia agents (e.g., taxol, actinomycin, bleomycin A2, mitomycin C, daunorubicin, doxorubicin, epirubicin, idarubicin, and mitoxantrone); soporific agents (e.g., zolpidem tartrate, eszopiclone, ramelteon, and zaleplon); tranquilizer agents (e.g., alprazolam, clonazepam, diazepam, flunitrazepam, lorazepam, triazolam, chlorpromazine, fluphenazine, haloperidol, loxapine succinate, perphenazine, prochlorperazine, thiothixene, and trifluoperazine); decongestant agents (e.g., ephedrine, phenylephrine, naphazoline, and tetrahydrozoline); beta blockers (e.g., levobunolol, pindolol, timolol maleate, bisoprolol, carvedilol, and butoxamine); alpha blockers (e.g., doxazosin, prazosin, phenoxybenzamine, phentolamine, tamsulosin, alfuzosin, and terazosin); non-steroidal hormones (e.g., corticotropin, vasopressin, oxytocin, insulin, oxendolone, thyroid hormone, and adrenal hormone); erectile disfunction improvement agents; herbal agents (e.g., *glycyrrhiza*, aloe, garlic, nigella *sativa*, rauwolfia, St John's wort, and valerian); enzymes (e.g., lipase, protease, amylase, lactase, lysozyme, and urokinase); humoral agents (e.g., prostaglandins, natural and synthetic, for example, PGE1, PGE2alpha, PGF2alpha, and the PGE1 analog misoprostol); psychic energizers (e.g., 3-(2-aminopropy)indole and 3-(2-aminobutyl)indole); nutritional agents; essential fatty acids; non-essential fatty acids; vitamins; minerals; and combinations thereof.

Any of the above-mentioned APIs may be incorporated in the composition described herein in any suitable form, such as, for example, as a pharmaceutically acceptable salt, uncharged or charged molecule, molecular complex, solvate or hydrate, prodrug, and, if relevant, isomer, enantiomer, racemic mixture, and/or mixtures thereof. Furthermore, the API may be in any of its crystalline, semi-crystalline, amorphous, or polymorphous forms.

In one embodiment, the API present in the pharmaceutical composition may have a potential for abuse. For example, the API may be an opioid analgesic agent, a stimulant agent, a sedative agent, a hypnotic agent, an antianxiolitic agent, or a muscle relaxing agent.

In another embodiment, the API present in the pharmaceutical composition may be a combination of an opioid analgesic and a non-opioid analgesic. Suitable opioid and non-opioid analgesics are listed above.

In a preferred embodiment, the API in the pharmaceutical composition may be an opioid analgesic. Exemplary opioid analgesics include oxycodone, oxymorphone, hydrocodone, hydromorphone, codeine, and morphine. In one exemplary embodiment, the API may be oxycodone hydrochloride. In another exemplary embodiment, the API may be oxymorphone hydrochloride.

The amount of the API in the pharmaceutical composition can and will vary depending upon the active agent. In embodiments in which the API is an opioid analgesic, the amount of opioid in the composition may range from about 2 mg to about 160 mg. In various embodiments, the amount of opioid in the pharmaceutical composition may range from about 2 mg to about 10 mg, from about 10 mg to about 40 mg, from about 40 mg to about 80 mg, or from about 80 mg to about 160 mg. In certain embodiments, the amount of opioid in the pharmaceutical composition may be about 5 mg, 7.5 mg, 10 mg, 12.5 mg, 15 mg, 17.5 mg, 20 mg, 22.5 mg, 25 mg, 27.5 mg, 30 mg, 32.5 mg, 35 mg, 37.5 mg, 40 mg, 45 mg, 50 mg, 60 mg, 70 mg, 80 mg, 100 mg, 120 mg, 140 mg, or 160 mg.

In embodiments in which the opioid is oxycodone hydrochloride, the total amount of oxycodone hydrochloride present in the pharmaceutical composition may range from about 2 mg to about 80 mg. In certain embodiments, the amount of oxycodone hydrochloride in the pharmaceutical composition may range from about 2 mg to about 10 mg, from about 10 mg to about 30 mg, or from about 30 mg to about 80 mg. In exemplary embodiments, the amount of oxycodone hydrochloride present in the pharmaceutical composition may be about 5 mg, about 10 mg, about 15 mg, about 20 mg, about 30 mg, about 40 mg, about 60 mg, or about 80 mg.

In embodiments in which the opioid is oxymorphone hydrochloride, the total amount of oxymorphone hydrochloride present in the pharmaceutical composition may range from about 2 mg to about 80 mg. In certain embodiments, the amount of oxymorphone hydrochloride present in the pharmaceutical composition may range from about 2 mg to about 10 mg, from about 10 mg to about 30 mg, or from about 30 mg to about 80 mg. In preferred embodiments, the amount of oxymorphone hydrochloride present in the pharmaceutical composition may be about 5 mg, about 10 mg, about 20 mg, about 30 mg, or about 40 mg.

(vi) Lubricant

The pharmaceutical composition disclosed herein may also comprise a lubricant. Non-limiting examples of suitable lubricants include metal stearate such as magnesium stearate, calcium stearate, zinc stearate, colloidal silicon dioxide, hydrogenated vegetable oils, sterotex, polyoxyethylene monostearate, polyethylene glycol, sodium stearyl fumarate, sodium benzoate, sodium lauryl sulfate, magnesium lauryl sulfate, light mineral oil, and combinations thereof. In exemplary embodiments, the lubricant may be a metal stearate. In one exemplary embodiment, the lubricant may be magnesium stearate.

The amount of lubricant present in the pharmaceutical composition can and will vary depending upon the identities and amounts of other components in the composition. In general, the amount of lubricant present in the composition may range from about 0.1% to about 3% by weight of the pharmaceutical composition. In various embodiments, the amount of lubricant present in the composition may range from about 0.1% to about 0.3%, from about 0.3 to about 1%, or from about 1% to about 3% by weight of the composition. In exemplary embodiments, the amount of lubricant present in the composition may range from about 0.0.1% to about 2% by weight of the pharmaceutical composition. In one exemplary embodiment, the amount of lubricant present in the composition may range from about 0.3% to about 1% by weight of the pharmaceutical composition.

(vii) Optional Excipients

In various embodiments, the pharmaceutical compositions disclosed herein may further comprise at least one additional pharmaceutically acceptable excipient. Non-limiting examples of suitable excipients include clay minerals, binders, fillers, diluents, antioxidants, chelating agents, flavoring agents, coloring agents, taste masking agents, and combinations thereof.

In one embodiment, the excipient may be a clay mineral. A clay mineral refers to a hydrated aluminum phyllosilicate or a hydrated magnesium silicate comprising small insoluble particles. Mixing a clay mineral with a suitable solvent forms a colloidal dispersion of small particles that do not sediment. Non-limiting examples of suitable clay minerals include talc, bentonites, kaolinites, nontronites, montmorillonites, pyrophyllites, saponites, sauconites, vermiculites, and combinations thereof. In one iteration, the clay mineral may be powdered talc or micronized talc.

In a further embodiment, the excipient may be a binder. Suitable binders include, but are not limited to, starches, pregelatinized starches, gelatin, polyvinylpyrolidone, cellulose, methylcellulose, sodium carboxymethylcellulose, ethylcellulose, polyacrylamides, polyvinyloxoazolidone, polyvinylalcohols, C12-C18 fatty acid alcohol, polyethylene glycol, polyols, saccharides, oligosaccharides, polypeptides, peptides, and combinations thereof.

In another embodiment, the excipient may be a filler. Suitable fillers include carbohydrates, inorganic compounds, and polyvinylpyrrolidone. In some embodiments, the filler may be calcium sulfate, calcium phosphate, calcium silicate, microcrystalline cellulose, starch, modified starches, lactose, sucrose, mannitol, sorbitol, or combinations thereof.

In another embodiment, the excipient may include a diluent. Non-limiting examples of diluents suitable for use include pharmaceutically acceptable saccharides such as sucrose, dextrose, lactose, microcrystalline cellulose, fructose, xylitol, and sorbitol; polyhydric alcohols; starches; pre-manufactured direct compression diluents; and mixtures of any of the foregoing.

In yet another embodiment, the excipient may be an antioxidant. Suitable antioxidants include, without limit, ascorbyl palmitate, butylated hydroxyanisole, a mixture of 2 and 3 tertiary-butyl-4-hydroxyanisole, butylated hydroxytoluene, sodium isoascorbate, dihydroguaretic acid, potassium sorbate, sodium bisulfate, sodium metabisulfate, sorbic acid, potassium ascorbate, vitamin E, 4-chloro-2,6-ditertiarybutylphenol, alphatocopherol, propylgallate, and combinations thereof.

In an alternate embodiment, the excipient may be a chelating agent. Non-limiting examples of suitable chelating agents include ethylenediamine tetracetic acid (EDTA) and its salts, N-(hydroxy-ethyl)ethylenediaminetriacetic acid, nitrilotriacetic acid (NIA), ethylene-bis(oxyethylene-nitrilo) tetraacetic acid, 1,4,7,10-tetraazacyclodo-decane-N,N',N'',N'''-tetraacetic acid, 1,4,7,10-tetraaza-cyclododecane-N,N',N''-triacetic acid, 1,4,7-tris(carboxymethyl)-10-(2'-hydroxypropyl)-1,4,7,10-tetraazocyclodecane, 1,4,7-triazacyclonane-N,N',N''-triacetic acid, 1,4,8,11-tetraazacyclotetra-decane-N,N',N'',N'''-tetraacetic acid; diethylenetriamine-pentaacetic acid (DTPA), ethylenedicysteine, bis(aminoethanethiol)carboxylic acid, triethylenetetraamine-hexaacetic acid, 1,2-diaminocyclohexane-N,N,N', N'-tetraacetic acid, and combinations thereof.

In a further embodiment, the excipient may be a flavoring agent. Flavoring agents may be chosen from synthetic flavor oils and flavoring aromatics and/or natural oils, extracts from plants, leaves, flowers, fruits, and combinations thereof.

In still another embodiment, the excipient may be a coloring agent. Suitable color additives include food, drug and cosmetic colors (FD&C), drug and cosmetic colors (D&C), or external drug and cosmetic colors (Ext. D&C).

In yet another embodiment, the excipient may be a taste-masking agent. Taste-masking materials include cellulose ethers; polyethylene glycols; polyvinyl alcohol; polyvinyl alcohol and polyethylene glycol copolymers; monoglycerides or triglycerides; acrylic polymers; mixtures of acrylic polymers with cellulose ethers; cellulose acetate phthalate; and combinations thereof.

The amount of the one or more additional excipients in the composition can and will vary depending upon the identity of the excipient and the identities and amounts of the other components of the composition.

(viii) Optional Film Coating

In some embodiments, the pharmaceutical composition may further comprise an optional film coating. Typically, the film coating comprises at least one hydrophilic polymer and the coating does not affect the immediate release or tamper resistant properties of the composition. The film coating may provide moisture protection, enhanced appearance, increased mechanical integrity, improved swallowability, improved taste, and/or masking of odors.

Film coatings are well known in the art, e.g., they are commercially available under the tradename OPADRY®. Typically, a film coating comprises at least one hydrophilic polymer and at least one plasticizer. Non-limiting examples of suitable polymers include hydroxypropylmethy cellulose, hydroxypropyl cellulose, hydroxypropyl ethylcellulose, ethylcellulose, methylcellulose, cellulose acetate phthalate, microcrystalline cellulose and carrageenan, acrylic polymers, polyvinyl alcohol, anionic and cationic polymers of methacrylic acid, copolymers of methacrylates, copolymers of acrylates and methacrylates, copolymers of ethacrylate and methylmethacrylate, polyvinylacetate phthalate, and shellac. Examples of suitable plasticizers include, without limit, triethyl citrate (TEC), acetyltriethyl citrate (ATEC), acetyl tri-n-butyl citrate (ATBC), dibutyl sebacate, diethyl phthalate, and triacetin. The film coating may optionally comprise additional agents such as a coloring agent, a filler, a flavoring agent, a taste-masking agent, a surfactant, an anti-tacking agent, and/or an anti-foaming agent. Suitable examples of these agents are well known in the art and/or are detailed above.

(ix) Exemplary Embodiments

In exemplary embodiments, the pharmaceutical composition comprises from about 20% to about 35% by weight of a low molecular weight hydrophilic polymer having an average molecular weight of no more than about 200,000 Da; the low molecular weight comprising polyethylene oxide, hydroxypropylmethyl cellulose, and sodium carboxymethyl cellulose; about 2% to about 10% by weight of a high molecular weight hydrophilic polymer having an average molecular weight of at least about 400,000 Da; the high molecular weight polymer comprising polyethylene oxide and xanthan gum; about 50% to about 70% by weight of an effervescent system comprising an acid component and a base component; and an API chosen from oxycodone, oxymorphone, hydrocodone, hydromorphone, codeine, and morphine.

(b) Dosage Forms

The physical form of the pharmaceutical composition disclosed herein can and will vary. In general, the pharmaceutical composition is a solid dosage form. The solid dosage form may be one of various solid dosage units. Non-limiting examples of suitable solid dosage units include tablets, compacts, pellets, caplets, pills, and capsules. Such dosage units may be prepared using conventional methods known to those in the field of pharmaceutical formulation and described in the pertinent texts, e.g., in Gennaro, A. R., editor. "Remington: The Science & Practice of Pharmacy", 21st ed., Williams & Williams, and in the "Physician's Desk Reference", 2006, Thomson Healthcare. In general, the solid dosage form is formulated for oral administration.

In certain embodiments, the solid dosage unit may be a tablet. Non-limiting types of tablets include coated tablets, uncoated tablets, compressed tablets, compacted tablets, molded tablets, layered tablets, bilayer tablets, extruded tablets, multiparticle tablets, monolithic tablets, and matrix tablets. In exemplary embodiments, the pharmaceutical composition may be a solid dosage form comprising a tablet.

In embodiments in which the solid dosage form is a tablet, the tablet generally has a friability of no greater than about 1.0%. In certain embodiments, the tablet may have a friability of less than about 1.0%, less than about 0.5%, less than about 0.3%, less than about 0.2%, less than about 0.1%, less than about 0.05%, or less than about 0.01%. In exemplary embodiments, the tablet has a friability of zero.

(c) In Vitro Release Properties of the Composition

The solid dosage pharmaceutical composition disclosed herein is formulated such that the API in the composition is released rapidly. Thus, the composition is termed an immediate release composition. As used herein, "immediate release" generally refers to an average release of at least 70% of the API within 45 minutes in water. Unlike many immediate release compositions, the pharmaceutical composition disclosed herein comprises a blend of high molecular weight and low molecular weight hydrophilic polymers. The disclosed composition, however, also comprises an effervescent system that facilitates dissolution and rapid release of the API.

The in vitro dissolution of the API from the composition disclosed herein may be measured using an USP-approved release procedure. For example, dissolution may be measured using an USP Type 2 paddle apparatus, at a paddle speed of 50 rpm or 100 rpm, and a constant temperature of 37±0.5° C. The dissolution procedure may be performed in the presence of 500 mL, 900 mL, or 1,000 mL of a suitable dissolution medium (e.g., having a pH from 1.0 to 6.8). Non-limiting examples of suitable dissolution media include water, phosphate buffer (pH 6.8), acetate buffer (pH 4.5), and 0.1N HCl.

The pharmaceutical compositions disclosed herein provide immediate release of the API. In some embodiments, the pharmaceutical composition may have an average release of about 50%, 55%, 60%, 65%, 70%, 75%, 80%, 85%, 90%, 95%, or 99% of the API within 45 minutes. In other embodiments, the pharmaceutical composition may have an average release of about 50%, 55%, 60%, 65%, 70%, 75%, 80%, 85%, 90%, 95%, or 99% of the API within 30 minutes.

(d) Abuse Deterrent Properties of the Composition

The solid dosage pharmaceutical compositions disclosed herein also have abuse deterrent features. The blend of hydrophilic polymers and the effervescent system imparts sufficient mechanical integrity (i.e., strength, hardness, etc.) to the solid dosage form such that it is resistant to crushing, grinding, cutting, or pulverizing to form a powder comprising small particles. Additionally, because some of the hydrophilic polymers of the composition are gelling polymers, contact with a small volume of a suitable solvent leads to the formation of a viscous mixture or gel.

The mechanical integrity of the solid dosage pharmaceutical composition may be assessed by measuring the hardness or crushing strength of the solid dosage form. Hardness of the solid dosage form may be measured using any of numerous hardness testers, which are well known in the art. In general, the solid dosage composition has a hardness or crushing strength of at least 10 kilopond (kp). In various embodiments, the solid dosage composition may have a hardness or crushing strength ranging from about 10 kp to about 20 kp, from about 20 kp to about 30 kp, from about 30 kp to about 40 kp, or more than about 40 kp. In certain embodiments, the hardness or crushing strength of solid dosage composition is less than about 50 kp.

The mechanical integrity of the solid dosage pharmaceutical composition also may be assessed by measuring the particle size distribution after crushing, grinding, or pulverizing the composition in a suitable apparatus for a specified period of time. The solid dosage composition may be crushed, ground, or pulverized in a high-shear mill, a ball mill, a co-mill, pill crusher, a tablet grinder, a coffee grinder, a blender, a hammer, or another apparatus to reduce particle size. In embodiments in which the solid dosage composition is subjected to 6 minutes of milling in a high shear mill to form particles, more than 20%, 30%, 40%, 50%, 60%, 70%, 80%, 90%, or 95% of the particles have an average diameter of at least about 250 microns. In embodiments in which the solid dosage composition is placed between two metal (i.e., aluminum) pans or two pieces of aluminum foil and struck ten times with a hammer, more than 20%, 30%, 40%, 50%, 60%, 70%, 80%, 90%, or 95% of the particles have an average diameter of at least about 250 microns. Because the pharmaceutical composition disclosed herein is resistant to forming a fine powder by crushing, grinding or pulverizing, it deters abuse by inhalation.

Additionally, the pharmaceutical composition disclosed herein, whether whole, flattened, broken, crushed, or pulverized, forms a viscous mixture or gel when in contact with a small volume of a suitable solvent. The volume may be about 3 mL, 5 mL, or 10 mL. Suitable solvents include water, alcohols such as ethanol, acids such as acetic acid, fruit juice, and mixtures of any of the foregoing. The viscosity of the gel prevents the material from being drawn through an injection syringe needle. Consequently, the pharmaceutical compositions are resistant to abuse by extraction, filtering, and/or injection.

(II) Processes for Preparing Solid Dosage Pharmaceutical Compositions

Another aspect of the disclosure encompasses processes for preparing solid dosage forms of the pharmaceutical compositions disclosed herein. The processes comprise: (a) forming a mixture comprising at least one low molecular weight hydrophilic polymer, at least one high molecular weight hydrophilic polymer, and an effervescent system; (b) forming the mixture into a solid dosage unit; and (c) heating the solid dosage unit to form the solid dosage form. The solid dosage form optionally may be coated with a film coating.

(a) Forming a Mixture

The first step of the process comprises forming a mixture comprising the components of the pharmaceutical composition, which are detailed above in section (I)(a). The mixture comprises at least one hydrophilic polymer having an average molecular weight of no more than about 200,000 Da, at least one hydrophilic polymer having an average molecular weight of at least about 400,000 Da, an effervescent system comprising an acid component and a base component, and a lubricant. In general, the mixture further comprises at one API or a pharmaceutically acceptable salt thereof. The components may be combined in any order or may be premixed in various combinations before being combined together. For example, in one embodiment the acid component of the effervescent system may be co-processed with a polyalkylene glycol or Poloxamer prior to being mixed with the rest of the components. In another embodiment, the API may be combined with some of the components before being combined with the rest of the components. Thus, a variety of ordered mixing schemes are possible.

The mixture comprising the components of the composition may be formed by mixing, roller mixing, drum mixing, shear mixing, dry blending, chopping, milling, roller milling, granulating, dry granulating (e.g., slugging or roller compacting), wet granulating (e.g., fluid bed granulating, high shear granulating), and other mixing techniques known in the art.

(b) Forming a Solid Dosage Unit

The process further comprises forming the mixture from step (a) into a solid dosage unit. Suitable solid dosage units are described above in section (I)(b). Means of forming solid dosage units are well known in the art. In exemplary embodiments, the solid dosage unit may be a tablet. The tablet may be a compression tablet, a molded tablet, a compacted tablet, or a pressed tablet. In an exemplary embodiment, the tablet may be formed by direct compression. The shape of the tablet may vary. Non-limiting tablet shapes include round, oval, rectangular, and triangular. The size and mass of the tablet may vary. In various embodiments, the mass of the tablet may be range from about 100 mg to about 1000 mg. In exemplary embodiments, the mass of the tablet may range from about 300 mg to about 500 mg.

(c) Heating the Solid Dosage Unit

The process further comprises heating the solid dosage unit. This heating step dries and cures the solid dosage form, wherein the cured solid dosage form may have improved properties or characteristics relative to an uncured solid dosage unit (see Examples 1, 6-8, and 10 below). For example, the heating step may remove water from the solid dosage form, thereby protecting the effervescent system from premature effervescence. Additionally, the heating step may plasticize some of the polymers, thereby leading to increased resistance to crushing/pulverization and to more rapid release of the API.

In general, the heating step occurs at a temperature of less than about 90° C. In various embodiments, the solid dosage unit may be heated at a temperature from about 30° C. to about 35° C., from about 35° C. to about 40° C., from about 40° C. to about 45° C., from about 45° C. to about 50° C., from about 50° C. to about 55° C., from about 55° C. to about 60° C., from about 60° C. to about 65° C., from about 65° C. to about 70° C., from about 70° C. to about 75° C., from about 75° C. to about 80° C., from about 80° C. to about 85° C., or from about 85° C. to about 90° C. In exemplary embodiments, the heating temperature may range from about 50° C. to about 80° C.

The duration of the heating step can and will vary depending upon the components of the composition and the heating temperature. The duration of the heating step may range from about 10 minutes to about 10 hours. In general, the higher the temperature, the shorter the duration of time for the heating step. In an exemplary embodiment, the solid dosage unit may be heated to a temperature from about 65° C. to about 75° C. for a period of time ranging from about 1 hour to about 2 hours.

(d) Optionally Coating the Solid Dosage Form

The solid dosage form may be coated with a film coating. Suitable film coatings are detailed above in section (I)(a)(viii). In general, the solid dosage form may be coated with a film coating after the heating step.

DEFINITIONS

When introducing components of the embodiments described herein, the articles "a", "an", "the" and "said" are intended to mean that there are one or more of the elements. The terms "comprising", "including" and "having" are intended to be inclusive and mean that there may be additional components other than the listed components.

If the components described herein have asymmetric centers, all chiral, diastereomeric, racemic forms and all geometric isomeric forms of a structure are intended, unless the specific stereochemistry or isomeric form is specifically indicated.

Having described the invention in detail, it will be apparent that modifications and variations are possible without departing from the scope of the invention defined in the appended claims.

EXAMPLES

The following examples are included to illustrate, but not to limit the claimed pharmaceutical compositions and processes for making them.

Example 1. Immediate Release Formulation

Table 1 describes the formulation made in this example. The batch size was 1000 g. All the ingredients were first sieved through a US Standard 30 mesh screen. An 8-qt V-blender was charged with all the ingredients except the lubricant and blended for 15 minutes. Magnesium stearate was then added and blended for 3 minutes. Round tablets (diameter: 0.3125") were made from the blend using a Manesty Beta press. The tablets were cured by heating in an air oven for 2 hours. Two curing temperatures were tried (~65° C. and ~80° C.).

TABLE 1

Composition of formulation made in Example 1.

| Component | Mg/tablet | % weight |
| --- | --- | --- |
| Oxycodone hydrochloride | 15.7 | 8.49 |
| L-(+) Tartaric acid | 37.6 | 20.32 |
| Sodium bicarbonate | 42.2 | 22.81 |
| Polyox 100K (WSR N-10) | 38.0 | 20.54 |
| Polyox 4 Million (WSR 301NF) | 19.5 | 10.54 |
| Klucel HXF | 19.0 | 10.27 |
| Talc | 10.0 | 5.41 |
| Pluronic F127 | 2.0 | 1.08 |
| Magnesium stearate | 1.0 | 0.54 |
| Total | 185.0 | 100.00 |

The cured tablets were evaluated for hardness and dissolution. Hardness was determined using a hardness tester. The dissolution parameters were: USP Apparatus Type 2 (paddles) at 50 rpm. The temperature was 37°±0.5° C. The dissolution medium was 500 mL water. At specified times, samples were withdrawn from the dissolution tester and analyzed for oxycodone hydrochloride by an HPLC method. The percent of oxycodone released was calculated based on the amount in the formulation. The data are reported in Table 2.

TABLE 2

Properties of tablets made per Example 1.

| | Uncured | Cured at 65° C. for 2 hours | Cured at 80° C. for 2 hours |
| --- | --- | --- | --- |
| Mean Hardness (kp) | 5.4 kp | 17.6 kp | 13.0 kp |
| % of oxycodone HCl release at 30 minutes | 77.1 | 99.9 | 93.5 |

Example 2. Formulations with Varying Polymer Ratios

This example gives formulations consisting of oxycodone hydrochloride, tartaric acid, sodium bicarbonate, Polyox N-10 (molecular weight 100,000), Polyox 301NF (molecular weight 4 million), Klucel HXF, and magnesium stearate. In order to determine the optimal ratio of the polymers, formulations were prepared in which the amounts of oxycodone hydrochloride, tartaric acid, sodium bicarbonate, and magnesium stearate were kept constant and the amounts of the other three ingredients were varied. Table 3 presents the generic formula and Table 4 gives the specific ratios of the polymers for each formulation.

The batch size was 10-15 g. The required amounts were weighed individually, placed in a plastic bag, and mixed manually for about 5 minutes. Tablets were made by weighing the required amount, filling the die of a single-station Carver press, and compressing it at the desired force. The tablets were placed in aluminum pans and cured for 2 hours at ~65° C. in an air oven. After curing, the tablets were allowed to come to room temperature and characterized by dissolution in water. Samples were removed at 30 minutes and analyzed by HPLC for oxycodone hydrochloride. The percentage of oxycodone hydrochloride released from the formulation was determined.

TABLE 3

Composition of formulation made in Example 2.

| Component | Mg/tablet |
|---|---|
| Oxycodone hydrochloride | 15.73 |
| L-(+) Tartaric acid | 37.74 |
| Sodium bicarbonate | 42.37 |
| Polyox 100K (WSR N-10) | x |
| Polyox 4 Million (WSR 301NF) | y |
| Klucel HXF | z |
| Magnesium stearate | 0.92 |
| Total | 185.01 |

Note:
For values of x, y, and z consult Table 4. The sum of x, y, and z was 88.25 mg.

TABLE 4

Composition and properties of tablets made in Example 2

| | Formulation details (relative ratios) | | | % Oxycodone released at 30 min | |
|---|---|---|---|---|---|
| | Polyox 100K | Polyox 4 Million | Klucel HXF | | |
| ID | (x) | (y) | (z) | Uncured | Cured |
| EFF37-1 | 58.83 | 14.71 | 14.71 | 82.4 | 85.1 |
| EFF37-2 | 14.71 | 14.71 | 58.83 | 60.5 | 57.9 |
| EFF37-3 | 44.12 | 44.12 | 0.0 | 39.9 | 51.3 |
| EFF37-4 | 0.0 | 0.0 | 88.25 | 79.2 | 80.7 |
| EFF37-5 | 0.0 | 44.12 | 44.12 | 8.6 | 10.0 |
| EFF37-6 | 88.25 | 0.0 | 0.0 | 60.0 | 57.9 |
| EFF37-7 | 14.71 | 58.83 | 14.71 | 8.7 | 9.6 |
| EFF37-8 | 29.42 | 29.41 | 29.42 | 47.9 | 52.7 |
| EFF37-9 | 0.0 | 88.25 | 0.0 | 8.7 | 9.2 |
| EFF37-10 | 44.12 | 0.0 | 44.12 | 79.1 | 84.0 |

The data in Table 4 show that, in a few formulations, curing increased the release of oxycodone hydrochloride (API). A number of the formulations had unexpected results. For example, formulation EFF37-10, which contained Polyox 100K and Klucel (molecular weight: ~1 million) had greater release than formulation EFF37-6, which contained only Polyox 100K (molecular weight: 100,000). Moreover, formulation EFF37-1, which contained all three polymers, had higher release than formulation EFF37-6, which contained only Polyox 100K.

Example 3. Formulations Comprising Different Grades of Klucel

To determine whether other grades of Klucel could be used in place of Klucel HXF, formulations were prepared that contained Klucel MXF, Klucel GXF, or Klucel EXF. The formulations were prepared as described above in Example 2 by keeping constant the amounts of oxycodone hydrochloride, tartaric acid, sodium bicarbonate, and magnesium stearate while varying the other ingredients. In some formulations talc and/or Pluronic F127 were also included. Table 5 presents the relative ratios of the polymers and additional components, as well as the release of oxycodone from the formulations.

TABLE 5

Composition and properties of tablets made per Example 3.

| | Formulation details (relative ratios) | | | | | % Oxycodone released at 30 min | |
|---|---|---|---|---|---|---|---|
| | Polyox 100K | Polyox 4Million | Klucel type | Pluronic F127 | Talc | | |
| ID | (x) | (y) | (z) | | | Uncured | Cured |
| EFF38-1 | 14.71 | 14.71 | HXF (58.83) | 0.0 | 0.0 | 48.8 | 49.9 |
| EFF38-2 | 14.71 | 14.71 | MXF (58.83) | 0.0 | 0.0 | 50.6 | 56.6 |
| EFF38-3 | 14.71 | 14.71 | GXF (58.83) | 0.0 | 0.0 | 30.1 | 36.1 |
| EFF38-4 | 14.71 | 14.71 | EXF (58.83) | 0.0 | 0.0 | 42.7 | 36.2 |
| EFF38-5 | 14.71 | 14.71 | HXF (48.83) | 0.0 | 10.00 | 53.6 | 71.3 |
| EFF38-6 | 14.71 | 14.71 | HXF (46.83) | 2.00 | 10.00 | 67.2 | 88.0 |

Note:
x, y, and z have the same connotations as in Table 3.

The dissolution results showed that dissolution was lower in formulations containing Klucel GXF or Klucel EXF (EFF-38-3 and EFF38-4). This was unexpected because the molecular weights of GXF and EXF grades are less than those of HXF or MXF. It was also found that inclusion of talc or both talc and Pluronic increased the amount of API released (compare formulations EFF38-5 and EFF38-6 with EFF38-1). The increased release imparted by talc and Pluronic was especially noticeable in the cured tablets.

Example 4. Formulations Containing Other Low MW Polymers

To determine whether other low molecular weight polymers could substitute for Polyox 100K, formulations were prepared that contained polyethylene glycol (PEG 8000) or Pluronic F127 in place of Polyox 100K. The formulations were prepared and tested as in Example 2. Some formulations included talc. Table 6 details the formulations, as well as the release of oxycodone from the formulations.

TABLE 6

Composition and properties of tablets made per Example 4.

| | Formulation Details (relative ratios) | | | % Oxycodone released at 30 min | |
|---|---|---|---|---|---|
| | Low MW Polymer | Polyox 4 Million | Klucel HXF | | |
| ID | (x) | (y) | (z) | Talc | Uncured | Cured |
| EFF39-1 | Polyox 100K 14.71 | 14.71 | 58.83 | 0.0 | 44.3 | 31.4 |
| EFF39-2 | PEG 8000 14.71 | 14.71 | 58.83 | 0.0 | 76.7 | 80.9 |
| EFF39-3 | Pluronic F127 14.71 | 14.71 | 58.83 | 0.0 | 62.3 | 68.0 |
| EFF39-4 | Pluronic F127 14.71 | 14.71 | 48.83 | 10.00 | 80.2 | 75.0 |
| EFF39-5 | Pluronic F127 14.71 | 31.77 | 31.77 | 10.00 | 11.1 | 14.8 |

Note:
x, y, and z have the same connotations as in Table 3

The data in Table 6 show that PEG 8000 can give dissolution properties similar to Polyox 100K, but not Pluronic F127. It was discovered, however, that inclusion of talc along with Pluronic F127 increased the amount of release (see formulation EFF39-4).

Example 5. Formulations Comprising Acid Co-Processed with Kolliphor

Formulations comprising the acid and base components of an effervescent system are susceptible to premature effervescence under conditions of high humidity. Such formulations may have a reduced shelf-life and decreased stability. The following example details a method for processing the tartaric acid with Kolliphor P407 (Pluronic F127) to reduce the moisture sensitivity and lower the likelihood of premature effervescence. Tartaric acid was placed with Kolliphor P407 in a high-shear granulator fitted with a 25 L bowl. The ratio of tartaric acid to Kolliphor P407 was 18.1/1.0 (w/w). With continued mixing, the temperature was raised to 65° C. After the hot-melt process was complete, the bowl was cooled to room temperature and sieved through a 20 Mesh sieve screen. The material going through the screen was used to formulate the blend shown in Table 7.

The blend in Table 7 had a batch size of 2700 g and was made as follows. Tartaric acid co-processed with Kolliphor was mixed for 5 minutes with micronized talc in a 4-qt V-blender. This mixture was then blended for 15 minutes with the other ingredients except magnesium stearate in an 8-qt V-blender. The magnesium stearate was then added to the blender and mixed for 3 minutes. It should be noted that EfferSoda® 12 is heat-treated sodium bicarbonate with a thin layer of sodium carbonate on its surface. The final blend was compressed in a rotary tablet press (Manesty Beta press) to produce round tablets. The tablets were then cured for 2 hours at 60-65° C. in a pan coater.

TABLE 7

Composition of the formulation made in Example 5.

| Component | Mg/tab | % wt |
|---|---|---|
| Oxycodone HCl | 15.00 | 5.00 |
| Tartaric Acid co-processed with Kolliphor P407 | 94.34 | 31.45 |
| EfferSode ®12 | 105.66 | 35.22 |
| Polyox N10 LEO (100K) | 37.56 | 12.52 |
| Polyox WSR 301 NF LEO (4 Million) | 19.13 | 6.38 |
| Klucel HF | 19.13 | 6.38 |
| Micronized Talc (Pharma M) | 7.56 | 2.52 |
| Magnesium stearate | 1.62 | 0.54 |
| Total | 300.00 | 100.01 |

The hardness of the tablets before curing was 5.5 kp which increased to 14.4 kp at the end of the curing process. Dissolution of the oxycodone hydrochloride was 91.7% at 30 minutes.

Example 6. Formulations Comprising Additional Hydrophilic Polymers

It is possible to include other hydrophilic polymers in the formulation cited in Example 5. Table 8 gives two formulations (24-1 and 24-2), each having a batch size of ~2700 g. Both formulations used tartaric acid co-processed with Kolliphor as described in Example 5. Formulation 24-1 contained sodium carboxymethylcellulose and xanthan gum rather than Klucel HF. Formulation 24-2 contained sodium carboxymethylcellulose, xanthan gum, and Klucel HF. The blending, compression, and curing processes were as outlined in Example 5. Curing was effected by heating the tablets for 2 hours at 70-75° C.

TABLE 8

Composition of the formulations made in Example 6.

|  | Formulation 24-1 | | Formulation 24-2 | |
| --- | --- | --- | --- | --- |
| Component | Mg/tablet | % wt | Mg/tablet | % wt |
| Oxycodone Hydrochloride | 15.7 | 3.68 | 15.7 | 3.68 |
| Tartaric Acid co-processed with Kolliphor P407 | 141.5 | 33.30 | 132.1 | 31.08 |
| EfferSoda ®12 | 158.5 | 37.29 | 147.9 | 34.81 |
| Polyox N10 LEO (100K) | 52.0 | 12.24 | 52.0 | 12.24 |
| Polyox WSR 301 NF LEO (4 Mil) | 15.0 | 3.53 | 15.0 | 3.53 |
| Carboxymethyl cellulose, sodium | 20.0 | 4.71 | 20.0 | 4.71 |
| Klucel HF | 0.0 | 0.0 | 20.0 | 4.71 |
| Xanthan gum | 10.6 | 2.48 | 10.6 | 2.48 |
| Micronized Talc | 10.1 | 2.39 | 10.1 | 2.39 |
| Magnesium stearate | 1.6 | 0.38 | 1.6 | 0.38 |
| Total | 425.0 | 100.00 | 425.0 | 100.01 |

Hardness and dissolution data for the tablets are given in Table 9. These data show that formulations containing additional hydrophilic polymers retained good tablet hardness and excellent oxycodone release.

TABLE 9

Hardness and dissolution data for the tablets made per Example 6.

|  | Formulation 24-2 | | Formulation 24-1 | |
| --- | --- | --- | --- | --- |
|  | Uncured | Cured | Uncured | Cured |
| Mean hardness (kp) | ~5 | 17.6 | ~5 | 18.7 |
| Dissolution in water |  |  |  |  |
| 10 minutes | 45.1 | 78.7 | 53.7 | 94.0 |
| 20 minutes | 69.9 | 99.4 | 81.2 | 100.6 |

Example 7. Formulations Comprising Acid and Kolliphor with or without Co-Processing This example details the properties of two formulations (31-1 and 33-1). Formulation (31-1) was made with tartaric acid co-processed with Kolliphor while formulation 33-1 used tartaric acid and Kolliphor as received without co-processing. All the other components were the same as evident from Table 10. The batch size was ~6 kg and utilized a 16-qt V-blender, a rotary tablet press. Curing was performed at 70-75° C. in a pan coater. Both formulations were compressed to give oval tablets. Formulation details are given in Table 10 and the dissolution data are shown in Table 11.

TABLE 10

Composition of the formulations made in Example 7.

|  | Formulation 31-1 | | Formulation 33-1 | |
| --- | --- | --- | --- | --- |
| Component | Mg/tab | % wt | Mg/tab | % wt |
| Oxycodone Hydrochloride | 15.7 | 3.53 | 15.7 | 3.53 |
| Tartaric acid co-processed with Kolliphor P407 | 127.4 | 29.98 | 0.0 | 0.0 |
| L-(+)-Tartaric Acid | 0.0 | 0.0 | 120.73 | 28.41 |
| Kolliphor P407 | 0.0 | 0.0 | 6.67 | 1.57 |
| EfferSoda ®12 | 142.6 | 33.55 | 142.6 | 33.55 |
| Polyox N10 LEO (100K) | 52.7 | 12.40 | 52.7 | 12.40 |
| Polyox WSR 301 NF LEO (4 Mil) | 15.0 | 3.53 | 15.0 | 3.53 |
| Carboxymethyl cellulose, sodium | 20.0 | 4.71 | 20.0 | 4.71 |
| Hydroxypropylmethyl cellulose | 30.0 | 7.06 | 30.0 | 7.06 |
| Xanthan gum | 10.6 | 2.49 | 10.6 | 2.49 |
| Micronized Talc | 10.1 | 2.38 | 10.1 | 2.38 |
| Magnesium stearate | 1.6 | 0.38 | 1.6 | 0.38 |
| Total | 425.0 | 100.01 | 425.0 | 100.01 |

TABLE 11

Properties of tablets made per Example 7.

|  | Formulation 31-1 | Formulation 33-1 |
| --- | --- | --- |
| Mean hardness (kp) before curing | 6.1 | 8.1 |
| Mean hardness (kp) after curing | 23.7 | 26.8 |
| % Oxycodone released in water from cured tablets at 15 minutes | 93.6 | 93.8 |
| Abuse deterrence test: Milling for 6 minutes |  |  |
| % Particles >250 microns post milling | 73.22 | 91.89 |
| Abuse deterrence test: Hammering |  |  |
| % Particles >250 microns post-hammering | 87.38 | 93.9 |

Table 11 also gives results from two types of tests to determine the abuse deterrence characteristics of cured tablets. In the milling test, the tablets were ground for 6 minutes in a high-shear mill. Sieve analysis was performed on the resulting chunky product and the percent of coarse particles with size >250 microns was determined. In the hammering test, the tablets were placed between two aluminum pans and struck 10 times with a hammer. The resulting product was crushed between fingers. The particles size was then determined and the percent >250 microns was reported. Higher values from these tests were taken as indicators of abuse deterrence. This example revealed that formulation 33-1 had improved abuse deterrent properties.

Example 8. Formulations with and without Kolliphor and/or Talc

In this example, four formulations (33-1, 33-2, 33-3, and 33-4) were evaluated in which Kolliphor and/or talc were removed in some formulations. Table 12 gives the compositions in mg/tablet. The tartaric acid and Kolliphor were used as received without co-processing. The batches were ~1 kg in size and were made using a 4-qt blender. Oval tablets were made using a rotary tablet press and cured in a pan coater for 2 hours at ~72° C. The cured tablets were coated in a pan coater with Opadry coating materials marketed by Colorcon, Inc. The tablets were tested for hardness and dissolution. Comparing formulations 33-1 with 33-2, 33-3, and 33-4, it is clear that good dissolution characteristics may be achieved without Kolliphor and/or talc in the formulation.

TABLE 12

Compositions and properties of tablets made in Example 8.

| Component | 33-1 Mg/tab | 33-2 Mg/tab | 33-3 Mg/tab | 33-4 Mg/tab |
|---|---|---|---|---|
| Oxycodone Hydrochloride | 15.7 | 15.7 | 15.7 | 15.7 |
| L-(+)-Tartaric Acid | 120.73 | 120.73 | 120.73 | 120.73 |
| Kolliphor P407 | 6.67 | 0.0 | 7.17 | 0.0 |
| Micronized Talc | 10.1 | 10.6 | 0.0 | 0.0 |
| EfferSoda ®12 | 142.6 | 142.6 | 142.6 | 142.6 |
| Polyox N10 LEO (100K) | 52.7 | 54.5 | 55.9 | 58.7 |
| Polyox WSR 301 NF LEO (4 Mil) | 15.0 | 15.7 | 16.1 | 16.9 |
| Carboxymethyl cellulose, sodium | 20.0 | 21.0 | 21.5 | 22.6 |
| Hydroxypropylmethyl cellulose | 30.0 | 31.4 | 32.2 | 33.9 |
| Xanthan gum | 10.6 | 11.1 | 11.4 | 12 |
| Magnesium stearate | 1.6 | 1.7 | 1.7 | 1.8 |
| Total | 425.0 | 425.0 | 425.0 | 425.0 |
| Properties | | | | |
| Hardness of Uncured tablets (kp) | 8.12 | 8.32 | 9.9 | 13.2 |
| Hardness of Cured tablets (kp) | 26.8 | 23.4 | 18.4 | 28.4 |
| Hardness of Coated tablets (kp) | 28.0 | 25.8 | 19.8 | 30.7 |
| % Oxycodone released in water at 15 minutes | 93.8 | 93.6 | 95.1 | 90.2 |

Example 9. Further Formulation Modifications

Formulations in this example (37-7, 37-8, 37-9, and 37-10) were made in batch sizes of ~25 g by blending the components in plastic bags. The tartaric acid and Kolliphor were used as received without co-processing. Oval tablets were made using a single station press and cured in an air oven at ~70° C. for 2 hours. The cured tablets were evaluated by hardness and hammering. The results are summarized in Table 13. The performance of Kolliphor and PEG 3350 was comparable (Formulations 37-8 and 37-9). Formulation containing neither Kolliphor nor PEG 3350 also performed well (37-10). Formulations 37-8 and 37-7 differed in their content of Polyox 100K. Higher level of Polyox 100K in the formulation (37-7) gave better crush resistance as seen from the particle size data.

TABLE 13

Compositions and properties of tablets made in Example 9.

| Component | 37-7 Mg/tab | 37-8 Mg/tab | 37-9 Mg/tab | 37-10 Mg/tab |
|---|---|---|---|---|
| Oxycodone Hydrochloride | 31.3 | 31.3 | 31.3 | 31.3 |
| L-(+)-Tartaric Acid | 126.0 | 131.5 | 131.5 | 132.9 |
| Kolliphor P407, Micronized | 2.9 | 2.9 | 0.0 | 0.0 |
| Polyethylene glycol (PEG 3350) | 0.0 | 0.0 | 2.9 | 0.0 |
| EfferSoda ®12 | 148.9 | 155.3 | 155.3 | 156.9 |
| Polyox N10 LEO (100K) | 98.7 | 86.9 | 86.9 | 86.9 |
| Polyox WSR 301 NF LEO (4M) | 14.7 | 14.7 | 14.7 | 14.7 |
| Sodium carboxymethyl cellulose | 20.0 | 20.0 | 20.0 | 20.0 |
| Methocel K100M CR | 30.0 | 30.0 | 30.0 | 30.0 |
| Xanthan gum | 10.6 | 10.6 | 10.6 | 10.6 |
| Magnesium stearate | 1.9 | 1.9 | 1.9 | 1.9 |
| Total | 485.0 | 485.0 | 485.0 | 485.0 |
| Abuse Deterrent Properties | | | | |
| Mean hardness (kp) | 27.5 | 24.1 | 23.3 | 23.2 |
| % Particles >250 microns post-hammering | 94.2 | 91.1 | 94.5 | 92.7 |

Example 10. Additional Formulation Modifications

Formulations in this example were made using tartaric acid and PEG 3350 as received. The compositions are presented in Table 14. The batch size was 100 g. The blends were made in plastic bags and the tablets with a single station press. The tablets were cured in an oven at ~70° C. for 2 hours. The tablets were evaluated for oxycodone release and by abuse deterrence tests (see Table 14 for data).

TABLE 14

Compositions and properties of tablets made in Example 10.

| Component | 44-1 % wt | 44-5 % wt | 44-6 % wt | 44-7 % wt | 44-8 % wt | 44-9 % wt | 44-10 % wt |
|---|---|---|---|---|---|---|---|
| Oxycodone HCl | 6.41 | 6.41 | 9.24 | 8.66 | 7.33 | 7.15 | 8.07 |
| L-(+)-Tartaric Acid | 25.94 | 0.0 | 37.38 | 0.0 | 29.64 | 28.92 | 32.63 |
| KH$_2$PO$_4$ | 0 | 25.94 | 0.0 | 0.0 | 0.0 | 0.0 | 0.0 |
| EfferSoda ®12 | 30.62 | 30.62 | 0.0 | 41.34 | 34.99 | 34.14 | 38.52 |
| PEG 3350 | 0.60 | 0.60 | 0.86 | 0.81 | 0.68 | 0.67 | 0.75 |
| Polyox N10 LEO (100K) | 20.52 | 20.52 | 29.57 | 27.70 | 23.44 | 11.38 | 12.86 |
| Polyox WSR 301 NF LEO (4 Million) | 3.03 | 3.03 | 4.37 | 4.09 | 3.46 | 3.38 | 3.81 |
| Sodium carboxymethyl cellulose | 4.12 | 4.12 | 5.94 | 5.57 | 0.0 | 4.60 | 5.19 |
| Methocel K100M CR | 6.19 | 6.19 | 8.92 | 8.35 | 0.0 | 6.90 | 7.78 |
| Xanthan gum | 2.19 | 2.19 | 3.15 | 2.95 | 0.0 | 2.44 | 2.75 |
| Magnesium stearate | 0.39 | 0.39 | 0.56 | 0.53 | 0.45 | 0.44 | 0.49 |
| Total (%) | 100 | 100 | 100 | 100 | 100 | 100 | 100 |

TABLE 14-continued

Compositions and properties of tablets made in Example 10.

| Component | 44-1 % wt | 44-5 % wt | 44-6 % wt | 44-7 % wt | 44-8 % wt | 44-9 % wt | 44-10 % wt |
|---|---|---|---|---|---|---|---|
| Tablet weight (mg) | 485 | 485 | 344 | 366 | 408 | 431 | 376 |
| Properties |  |  |  |  |  |  |  |
| % drug released in water in 20 minutes |  |  |  |  |  |  |  |
| Uncured tablets | 81.9 | 97.7 | 11.7 | 1.8 | 99.2 | 72.0 | 23.5 |
| Cured tablets | 95.8 | 90.5 | 13.8 | 2.3 | 100.5 | 91.7 | 23.7 |
| Abuse Deterrence test (milling) |  |  |  |  |  |  |  |
| % Particles >250 microns post-milling | 68.5 | 47.9 | 85.9 | 44.2 | 72.2 | 55.8 | 9.3 |

The following conclusions were made from the data in Table 14: (i) Decreasing the level of PEO100K decreased dissolution in uncured tablets in spite of increasing effervescent agents (compare 44-9 and 44-1); (ii) Removing the gel-forming polymers increased dissolution (44-8); (iii) Removing the low molecular weight POLYOX (PEO 100K) decreased dissolution (44-10) and curing in this case did not increase dissolution; (iv) Data for formulations 44-6 and 44-7 show that both acid AND base components are necessary to achieve good dissolution, and (v) Tartaric acid, an organic acid may be substituted with an inorganic acid (Formulations 44-1 and 44-5).

What is claimed is:

1. A pharmaceutical composition comprising at least one active pharmaceutical ingredient (API) or a pharmaceutically acceptable salt thereof, about 15% to about 35% by weight of at least one low molecular weight hydrophilic polymer, about 1% to about 15% by weight of at least one high molecular weight hydrophilic polymer, and about 50% to about 70% by weight of an effervescent system, wherein the at least one low molecular weight hydrophilic polymer has an average molecular weight of no more than 200,000 Daltons, the at least one high molecular weight hydrophilic polymer has an average molecular weight of at least 400,000 Daltons, the pharmaceutical composition is a solid dosage form that has been heated at a temperature from about 50° C. to about 80° C. to plasticize and/or cure at least one of the low or high molecular weight hydrophilic polymers, and the solid dosage form provides immediate release of the at least one API and deters abuse by breaking into a plurality of particles having an average diameter of greater than about 250 microns rather than a fine powder when crushed, ground, or pulverized.

2. The pharmaceutical composition of claim 1, wherein the at least one low molecular weight hydrophilic polymer is chosen from a polyalkylene oxide, a cellulose ether, a polyalkylene glycol, a poloxamer, or combinations thereof.

3. The pharmaceutical composition of claim 1, wherein the at least one high molecular weight hydrophilic polymer is chosen from a polyalkylene oxide, a cellulose ether, a polysaccharide, or combinations thereof.

4. The pharmaceutical composition of claim 1, wherein the effervescent system comprises an a) acid component chosen from an organic acid, an inorganic acid, or combinations thereof and b) a base component chosen from an alkali metal bicarbonate, an alkaline earth metal bicarbonate, an alkali metal carbonate, an organic carbonate, or combinations thereof.

5. The pharmaceutical composition of claim 1, wherein the at least one API is an opioid or a combination of an opioid and a non-opioid analgesic, and the opioid is chosen from oxycodone, oxymorphone, hydrocodone, hydromorphone, codeine, or morphine.

6. The pharmaceutical composition of claim 1, which forms a viscous mixture or gel when in contact with a small volume of a suitable solvent.

7. The pharmaceutical composition of claim 1, wherein the solid dosage form has a hardness of at least about 15 kiloponds.

8. The pharmaceutical composition of claim 1, which releases at least about 80% of the at least one API within about 30 minutes when measured using an USP-approved in vitro release procedure.

9. The pharmaceutical composition of claim 1, wherein the at least one low molecular weight hydrophilic polymer is chosen from polyethylene oxide, hydroxypropylmethyl cellulose, sodium carboxymethyl cellulose, polyethylene glycol, a poloxamer, or combinations thereof; the at least one high molecular weight hydrophilic polymer is chosen from polyethylene oxide, xanthan gum, hydroxypropyl cellulose, hydroxypropylmethyl cellulose, or combinations thereof; the effervescent system comprises a) an acid component chosen from an organic acid, an inorganic acid, or combinations thereof and b) a base component chosen from an alkali metal bicarbonate, an alkaline earth metal bicarbonate, an alkali metal carbonate, an organic carbonate, or combinations thereof; and the at least one API is an opioid chosen from oxycodone, oxymorphone, hydrocodone, hydromorphone, codeine, or morphine.

10. The pharmaceutical composition of claim 9, wherein the at least one low molecular weight hydrophilic polymer comprises polyethylene oxide, hydroxypropylmethyl cellulose, and sodium carboxymethyl cellulose; and the at least one high molecular weight polymer comprises polyethylene oxide and xanthan gum.

11. The pharmaceutical composition of claim 10, wherein the effervescent system comprise tartaric acid and sodium bicarbonate.

12. The pharmaceutical composition of claim 9, wherein the solid dosage form has a hardness of at least about 20 kiloponds.

13. The pharmaceutical composition of claim 9, which releases at least about 80% of the at least one API within about 30 minutes when measured using an USP-approved in vitro release procedure.

14. The pharmaceutical composition of claim 13, which releases at least about 85% of the at least one API within about 30 minutes.

15. The pharmaceutical composition of claim 14, which releases at least about 90% of the at least one API within about 30 minutes.

16. The pharmaceutical composition of claim 15, which releases at least about 95% of the at least one API within about 30 minutes.

17. The pharmaceutical composition of claim 16, which releases at least about 99% of the at least one API within about 30 minutes.

18. The pharmaceutical composition of claim 1, wherein the solid dosage form is prepared by a process comprising:
   a) forming a mixture comprising the at least one active pharmaceutical ingredient (API) or a pharmaceutically acceptable salt thereof, about 15% to about 35% by weight of the at least one low molecular weight hydrophilic polymer with an average molecular weight of no more than 200,000 Daltons, about 1% to about 15% by weight of the at least one high molecular weight hydrophilic polymer with an average molecular weight of at least 400,000 Daltons and about 50% to about 70% by weight of the effervescent system;
   b) forming the mixture into a solid dosage unit; and
   c) heating the solid dosage unit at a temperature from about 50° C. to about 80° C. to yield the solid dosage form.

* * * * *